United States Patent [19]
Schuster

[11] 4,218,229
[45] Aug. 19, 1980

[54] SEPARATION OF ETHYLENE-CONTAINING HYDROCARBON MIXTURES BY LOW TEMPERATURE RECTIFICATION

[75] Inventor: Robert Schuster, Munich, Fed. Rep. of Germany

[73] Assignee: Linde Aktiengesellschaft, Weisbaden, Fed. Rep. of Germany

[21] Appl. No.: 931,577

[22] Filed: Aug. 7, 1978

[30] Foreign Application Priority Data

Aug. 6, 1977 [DE] Fed. Rep. of Germany ....... 2735588

[51] Int. Cl.² .............................................. F25J 3/02
[52] U.S. Cl. .......................................... 62/28; 62/40; 62/31
[58] Field of Search ................. 62/26, 28, 27, 40, 31

[56] References Cited
U.S. PATENT DOCUMENTS

| | | | |
|---|---|---|---|
| 2,567,461 | 9/1951 | Aicher | 62/40 |
| 2,600,110 | 6/1952 | Hachmuth | 62/27 |
| 3,509,728 | 5/1970 | Mercer et al. | 62/31 |

*Primary Examiner*—Norman Yudkoff
*Attorney, Agent, or Firm*—Millen & White

[57] ABSTRACT

In a low temperature rectification process for the separation of ethylene from a mixture of ethylene and ethane comprising separating the ethylene-containing mixture into a liquid reboiler fraction enriched in ethane and a gaseous head fraction enriched in ethylene; heating and compressing the head fraction; partially liquefying resultant compressed gaseous head fraction in indirect heat exchange with the reboiler fraction; expanding and recycling resultant condensed head fraction in part as reflux to the rectification; and withdrawing in part resultant condensed fraction as product ethylene, the improvement which comprises heating the liquid reboiler fraction, in part, in indirect heat exchange with a closed refrigerantion cycle, e.g., an ethylene cycle.

12 Claims, 1 Drawing Figure

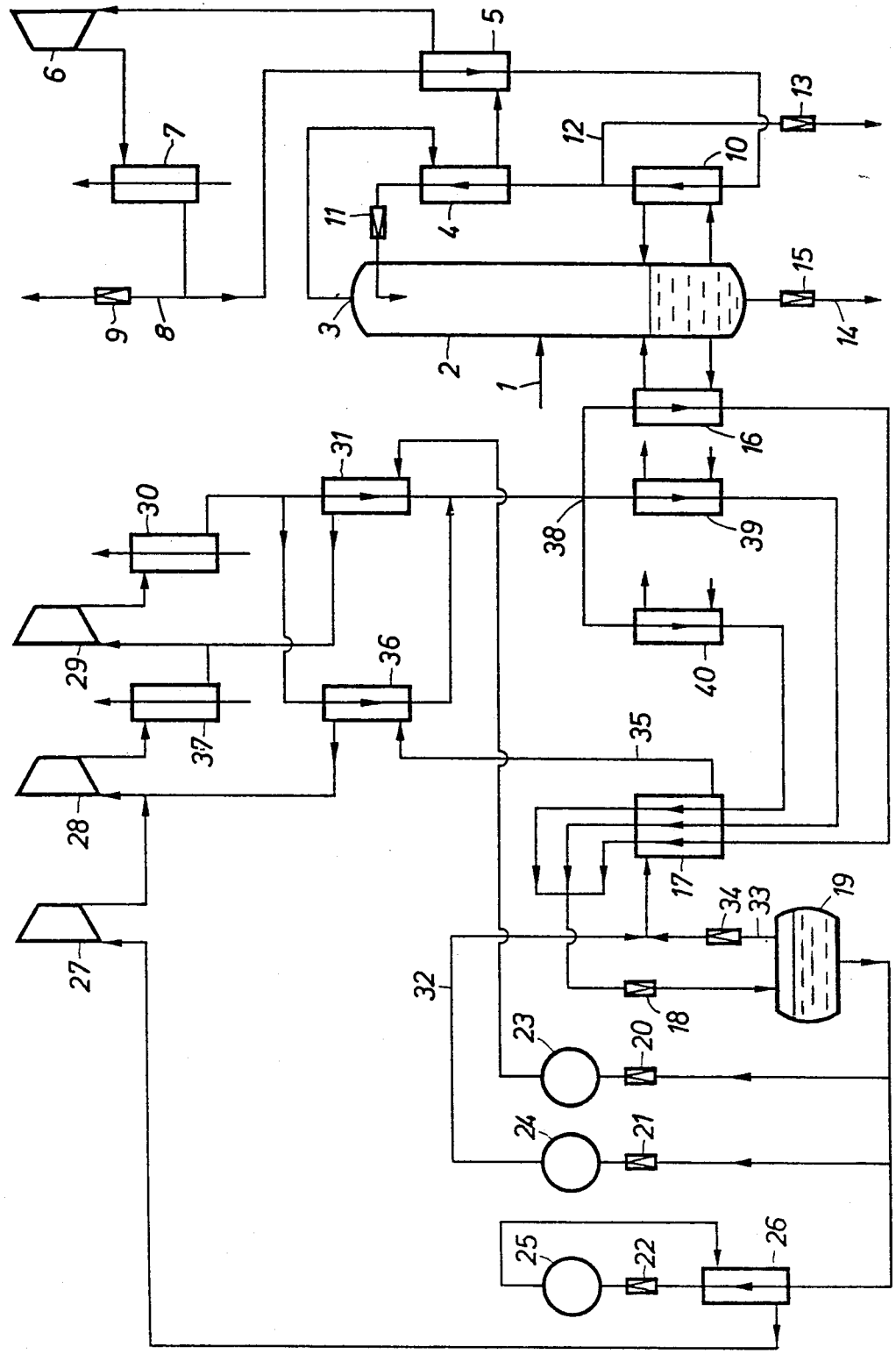

SEPARATION OF ETHYLENE-CONTAINING HYDROCARBON MIXTURES BY LOW TEMPERATURE RECTIFICATION

BACKGROUND OF THE INVENTION

This invention relates to a process for the separation of ethylene-containing hydrocarbon mixtures by rectivication at low temperatures. In particular, the invention relates to an improvement in a process wherein the ethylene-containing mixture is separated into a liquid reboiler fraction and an gaseous head fraction; the head fraction is heated, compressed, and partially liquefied in heat exchange with the reboiler fraction which is heated during this step. The resultant liquid is then expanded, and in part, returned as reflux to the rectification, and in part withdrawn as product ethylene.

An ethylene-ethane separation is normally a step at the end of a low-temperature process for the separation of hydrocarbons. The thermal conditions required for reboiler heating and head cooling in the ethylene column can be realized with the aid of a heat pump system. It is thus known from U.S. Pat. No. 3,260,057 to warm the part of the head gas of the ethylene column, to compress the heated gas, to cool the compressed gas countercurrently to itself, to condense cooled gas and to subcool resultant condensate, and then after expansion, to recycle the condensate into the ethylene column as reflux. The residual portion of the head product is withdrawn as gaseous ethylene.

A disadvantage of this conventional process is that the heating of the reboiler fraction takes place solely by liquefaction of the reflux. This means that there is little flexibility to operate and control the heat balance of this process.

OBJECT OF THE INVENTION

An object of this invention is to provide a system wherein the reboiler liquid can be heated in a substantially more effective fashion than heretofore.

Upon further study of the specification and appended claims, further objects and advantages of this invention will become apparent to those skilled in the art.

SUMMARY OF THE INVENTION

To attain the objects of this invention, the reboiler heat is provided, in part, by heat withdrawn from a closed refrigeration cycle. In this respect, it is preferred that about 0 % to 50 %, more preferably about 15 % to 35 % of the reboiler heat to be so provided with the remaining heat being provided by the head fraction recycled for reflux.

By this invention, advantage can be taken of the fact that in the low-temperature rectification of cracked gases into fractions of different boiling points there are normally present one or several refrigeration cycles. To conduct the process of this invention, it is thus merely necessary to alter an already existing refrigeration cycle -- such as the ethylene cycle -- for example by the use of further heat exchangers so that heat transfer is possible from the medium of the refrigerating cycle to the reboiler of the ethylene-ethane separation column. In this connection, a closed refrigeration cycle is employed in accordance with the invention; otherwise, mass transfer between the refrigeration cycle and the product-generating stage would have the disadvantage that impurities from the product-generating stage would enter the refrigeration cycle and would be able to comtaminate the medium of the refrigeration cycle and vice versa. A preferred ethylene closed refrigeration cycle operates at $-100°$ C. to $+120°C.$ and between 1.1 atm abs and 20 atm.abs. In all low temperature processes, cold will be generated and transported to various temperature levels via refrigeration cycles. The cold is mainly required to condense the feed gas and to provide the condenser duties for distillation columns operating below ambient temperature levels. The additional duty according to this invention is therefore a minor percentage of the total low temperature heat demand of the process. There are two basic principles of refrigeration cycles. The cascade principle and the mixed refrigerant cycle. In the cascade principle, there are various refrigerants, each with the ability to condense the other at a higher pressure level. A preferred cascade for example is cooling water - propylene - ethylene - methane. For the purpose of this invention, the most suitable cascade medium will be used, preferably ethylene or ethane in a mixed refrigerant compressor compressing a mixture of various components. The different temperature levels are obtained by partial evaporation of the mixture with different boiling points. For the purpose of this invention, also a mixed refrigerant cycle could be used, providing adequate heat duty to meet the reboiling requirements.

BRIEF DESCRIPTION OF DRAWING

The attached drawing is a schematic representation of a comprehensive preferred embodiment of the invention.

DETAILED DESCRIPTION OF DRAWING

At 1, 26,00 Nm$^3$/h. of a hydrocarbon mixture consisting of 25 % C$_2$H$_6$, 0.2 % C$_3$-hydrocarbons, and 74,8 % C$_2$H$_4$ is fed in partially condensed form at a temperature of $-45°$ C. into an ethylene column 2 which is under a pressure of 9 atmospheres absolute.

A gaseous hydrocarbon mixture consisting of 99.9 % C$_2$H$_4$ and 0.1 % CH$_4$ with C$_2$H$_6$ is withdrawn at 3 from the head of column 2, heated in heat exchangers 4 and 5 to $+25°$ C., and compressed in a compressor 5 from 8.5 atm. abs. to 20 atm. abs. Since the temperature of the mixture rises to 100° C. during this step, the mixture is cooled after compression to 30° C. in a heat exchanger 7 in heat exchange with water. At 8, 15,000 Nm$^3$/h. of the ethylene is discharged in the gaseous phase as product ethylene and expanded in 9. The remainder of ethylene is cooled in head exchanger 5 to $-25°$ C. and totally liquefied in a heat exchanger 10 by indirect heat exchange with liquid from the sump of the ethylene column 2. Most of the condensed ethylene is then subcooled in heat exchanger 4 and , after expansion in valve 11, returned to the head of ethylene column 2. The smaller proportion -- about 4,500 Nm$^3$/h. -- is withdrawn in the liquid phase at 12 as product ethylene and expanded in valve 13. If no liquid product ethylene is desired, a larger portion of product ethylene is instead withdrawn from the plant in the gaseous phase via valve 9.

At 14, 6,500 Nm$^3$/h. of hydrocarbons consisting of 99 % C$_2$H$_6$ and 1 % C$_2$H$_4$ with C$_3$-hydrocarbons is withdrawn from the sump of the ethylene column 2, said reboiler having a temperature of $-34°$ C. In valve 15, the reboiler product is expanded to 8 atm. abs. and conducted via conduit 14 to a plant -- not shown in the drawing -- for further processing, for example, to a thermal cracking reactor.

The reboiler of the ethylene column 2 is coupled via a heat exchanger 16 with a closed ethylene refrigeration cycle. Thereby the reboiler of the ethylene column is heated by compressed and condensing rectification overhead gas as well as by the ethylene refrigeration cycle.

Under conditions that so much of the product ethylene is withdrawn via valve 9, that there is an insufficiency of heat for heating the sump of the ethylene column 2, then the necessary makeup heat can now be provided by the closed ethylene refrigeration cycle.

The ethylene of the closed ethylene refrigeration cycle passes in parallel to heat exchanger 16 to further heat exchangers 39 and 40 wherein it is cooled to −40° C. in heat exchange with $C_3$-hydrocarbons or the reboiler product of a methane column -- the latter being not shown in the drawing. The refrigeration cycle ethylene, completely liquefied during this step, is subcooled in a heat exchanger 17 and expanded via valve 18 from a pressure of 20 atm. abs. to a pressure of 10 atm. abs. into a storage tank 19 for liquid ethylene.

(The term "refrigeration sink" is defined as a location in the process at which refrigeration is consumed at the desired low temperature level.)

Liquid ethylene is withdrawn from the storage tank 19 and expanded via valves 20, 21, and 22 to 9.5 atm. abs., 3 atm. abs., and 1.1 atm. abs., respectively, and is then conducted to refrigeration sinks 23, 24, and 25 wherein temperatures are ambient at −55° C., −80° C., and −100° C., respectively.

From the refrigeration sink 25, the refrigeration cycle ethylene flows via a heat exchanger 16, where it is heated counter-currently to itself to −70° C. In a compressor 27, the ethylene is compressed from 1 atm. abs. to 3 atm. abs. During this step, the temperature of the refrigeration cycle ethylene rises to about +40° C. A further compression stage follows with compressor 27, thus attaining a pressure of 8.5 atm. abs. To cool the refrigeration cycle ethylene, which has been heated to 120° C. on account of the compression, it is cooled in a heat exchanger 37 against water to a temperature of 30° C. A third compression stage follows wherein the refrigeration cycle ethylene is compressed from 8.5 atm. abs. to 20 atm. abs. The refrigeration cycle ethylene is again cooled in a heat exchanger 30 against water from 120° C. to 30° C. Downstream of heat exchanger 30, the refrigeration cycle ethylene is split into two partial streams and each stream is cooled in heat exchangers 31 and 36 respectively from 30° C. to −25° C. before being conducted to a branch- off point 38 from where the refrigeration cycle ethylene is liquefied in heat exchangers 16, 19 and 40.

Cooling in heat exchanger 36 takes place against refrigeration cycle ethylene coming from refrigeration sink 24 via conduit 32 and which is combined with the ethylene withdrawn from storage tank 19 via conduit 33 and expansion valve 34. This combined ethylene stream is conducted through heat exchanger 17 and via conduit 35 to heat exchanger 36. The resultant warmed combined stream is then passed to compressor 28 for compression from 3 atm. abs. to 8.5 atm. abs.

Cooling in heat exchanger 31 is realized by the refrigeration cycle ethylene withdrawn from refrigeration sink 23. After being heated in heat exchanger 31, the refrigeration cycle ethylene is conducted into compressor 29 for compression from 8.5 atm. abs. to 20 atm. abs.

The refrigeration sinks 23, 24, 25 represent feed gas coolers, where a stepwise condensation of the feed gas will be performed, to obtain a prefractionation of the hydrocarbons. In addition, they represent overhead condensers of the deethanizer, and other distillation or absorption towers operating at indicated temperature levels.

The preceding system can be repeated with similar success by substituting the generically or specifically described reactants and/or operating conditions of this invention for those used in the preceding system.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a low temperature rectification process for the separation of ethylene from a mixture of ethylene and ethane comprising feeding and separating the ethylene-containing mixture in a rectification column into a liquid reboiler fraction enriched in ethane and a gaseous head fraction enriched in ethylene; in a heat pump cycle heating and compressing the head fraction and partially liquefying resultant compressed gaseous head fraction in indirect heat exchange with the reboiler fraction and simultaneously heating said reboiler fraction; expanding and recycling resultant condensed heat fraction, in part, as reflux to the rectification column; and withdrawing, in part, resultant condensed fraction as product ethylene, the improvement which comprises heating the liquid reboiler fraction, in part, in indirect heat exchange with a closed refrigeration cycle, whereby said reboiler fraction is simultaneously heated by a combination of said heat pump cycle and said closed refrigeration cycle, said closed refrigeration comprising a compressor, a condenser in heat exchange with the reboiler fraction to condense the refrigerant, an expander for the condensate, and means to pass the expanded condensate in heat exchange with the condensate before ecpansion.

2. A process according to claim 1, wherein the closed refrigeration cycle is an ethylene cycle.

3. A process according to claim 2, wherein the ethylene cycle operates between −100° C. and +120° C.

4. A process according to claim 2 wherein the ethylene cycle operates between 1.1 atm. abs. and 20 atm. abs.

5. A process according to claim 1 wherein said process is an integral part of a larger process for separating hydrocarbons, and said refrigeration cycle is employed to yield refrigeration for liquefying and separating one or more gases other than ethylene and ethane.

6. A process according to claim 1 wherein said one or more gases have a boiling point lower than ethylene.

7. A process according to claim 6 wherein said one or more gases comprises methane.

8. A process according to claim 7 wherein the closed refrigeration cycle is an ethylene cycle.

9. A process according to claim 8 wherein said hydrocarbons are cracked hydrocarbons.

10. A process according to claim 9 wherein said closed refrigeration cycle is an ethylene cycle operating at −100° C. to +20° C. and 1.1 to 20 atmospheres absolute.

11. A rectification process as defined by claim 1, wherein said rectification column is a single rectification column operated at a substantially uniform pressure.

12. A rectification process according to claim 1, wherein said closed refrigeration cycle accounts for about 15–35% of the reboiler heat.

* * * * *